US00PP18545P3

(12) United States Plant Patent
Jewell

(10) Patent No.: US PP18,545 P3
(45) Date of Patent: Mar. 4, 2008

(54) **VARIETY OF *CORDYLINE* PLANT NAMED 'JEL01'**

(50) Latin Name: *Cordyline australis*
Varietal Denomination: Jel01

(76) Inventor: Geoff Jewell, 163 Settlement Rd, R.D, Otaki (NZ)

( * ) Notice: Subject to any disclaimer, the term of this patent is extended or adjusted under 35 U.S.C. 154(b) by 0 days.

(21) Appl. No.: 11/355,443

(22) Filed: Feb. 16, 2006

(65) Prior Publication Data

US 2006/0200885 P1 Sep. 7, 2006

(30) Foreign Application Priority Data

Mar. 7, 2005 (AU) ..... 2005/063

(51) Int. Cl.
*A01H 5/00* (2006.01)

(52) U.S. Cl. ..... Plt./383

(58) Field of Classification Search ..... Plt./263, Plt./383, 373
See application file for complete search history.

(56) References Cited

PUBLICATIONS

"Sunset Western Garden Book" p. 240, 1995. (3 pages total).*

* cited by examiner

*Primary Examiner*—Kent Bell
*Assistant Examiner*—S. B. McCormick-Ewoldt
(74) *Attorney, Agent, or Firm*—Fulwider Patton LLP

(57) ABSTRACT

A new and distinct cultivar of *Cordyline* plant named 'Jel01' characterized by burgundy foliage and a relatively short internode length.

1 Drawing Sheet

CROSS-REFERENCES TO RELATED APPLICATIONS

This application claims priority under 35 U.S.C. § 119 based on Australian Plant Breeders Rights Application No. 2005/121, filed Mar. 7, 2005.

BACKGROUND OF THE NEW PLANT

The present invention relates to a new and distinct cultivar of *Cordyline* plant, botanically known as *Cordyline australis,* and further known by the varietal name 'Jel01'. This new variety is also sold under the trade name Burgundy Spire (Breeder's Ref. No. CorJel01). The new variety was discovered from open pollination of a *Cordyline australis* 'Purpurea' by the inventor, Geoff Jewell, in Otaki, New Zealand in 2001. The parental cultivar is believed to be a *Cordyline australis* 'Purpurea' (unpatented). Seedlings grown from the parental cultivar seeds were planted out and plants with desirable ornamental characteristics were selected. The cultivar was isolated by the inventor in Otaki, New Zealand by seedling selection primarily on the basis of upright growth habit, foliage color, and suitability as a garden or container grown plant.

During the initial phases of discovery, asexual propagation was conducted via cuttings to establish a suitable population. Repeated generations established that the cultivar was stable. Subsequently, the cultivar was propagated asexually by tissue culture with several generations in New Zealand and several generations in Australia (minimum of two generations) and has been found to be stable with no recorded off types. Continued observation of future generations have confirmed that the distinguishing features of this new cultivar came true, remain stable and are retained through successive propagation.

The closest comparator to 'Jel01' known to applicant is *Cordyline australis* 'Red Sensation' (unpatented) which is an erect plant with red/brown foliage. The parent *C. australis* 'Purpurea' has bronze foliage.

SUMMARY OF THE INVENTION

Plants of the cultivar 'Jel01' have not been observed under all possible environmental and cultural conditions. The phenotype of the new cultivar may vary somewhat with variations in environment such as temperature, light intensity, length of day, irrigation amount and frequency, and/or fertilizer rate without, however, any variance in genotype.

The following traits have been repeatedly observed and are determined to be among the unique characteristics of 'Jel01'. These characteristics distinguish 'Jel01' as a new and distinct cultivar from its closest comparator *Cordyline australis* 'Red Sensation':

1. Burgundy foliage.

Compared to other plants of the *Cordyline* genus, the new *Cordyline* has a distinctive burgundy foliage.

BRIEF DESCRIPTION OF THE DRAWINGS

The invention is depicted in the accompanying colored photographs in which.

Figure 1:
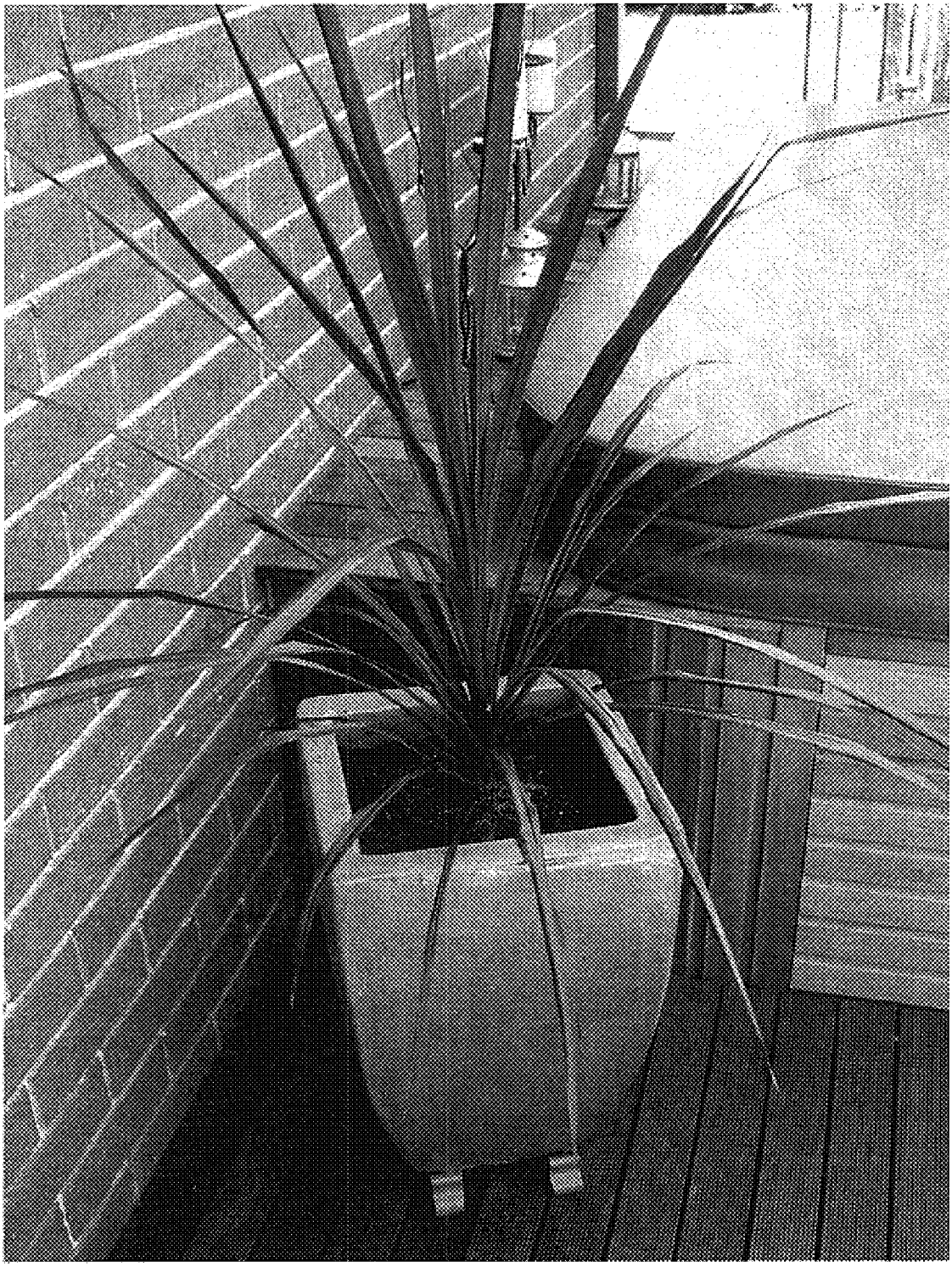
FIG. 1 shows a potted plant illustrating the characteristic foliage.

The photograph depicts the overall appearance of the new *Cordyline,* showing the colors as true as it is reasonably possible to obtain in colored reproductions of this type. Colors in the photograph may differ slightly from the color values cited in the Detailed Botanical Description which more accurately describe the actual colors of the new *Cordyline*.

DETAILED BOTANICAL DESCRIPTION OF THE NEW PLANT

The following detailed description sets forth characteristics of the new cultivar. The data which defines each characteristic was collected from reproductions of the plant grown in an open greenhouse. The plant histories of *Cordyline* 'Jel01' were taken on multiple pots containing single plants.

In the following table of plant characteristics, color references are made to The Royal Horticultural Society of London Colour Chart, 1995 Edition. The age of the plant described is approximately 1½ years old with measurements taken from mature leaves.

THE PLANT

Classification:

*Botanical.*—*Cordyline australis.*
*Varietal name.*—'Jel01'.
*Parentage.*—*Cordyline australis.*
*Asexual propagation.*—Tissue culture.

Form:

*Plant growth rate.*—Moderate to fast.
*Growth habit.*—Upright.
*Plant density.*—Bushy around central stem.
*Growth type.*—Erect.
*Mean plant height.*—750 mm at age 1½ years.
*Mean plant width.*—250 mm at age 1½ years.

Stem:

*Scapes.*—Basal foliage.
*Mean stem diameter.*—20 mm.
*Mean stem length.*—2000 mm.

Leaves:

*Leaf color.*—Burgundy.
*Leaf shape.*—Sword-shaped.
*Mean leaf width (mm).*—24 mm.
*Mean leaf length (mm).*—880 mm.

Leaf characteristics:

*Apex.*—Acute.
*Margin.*—Slight undulations.
*Length.*—750 mm (from horizontal leaves in mid section).
*Width.*—52 mm at widest section.
*Texture.*—Glossy upper side, non-glossy lower side.
*Shape.*—Sword-shaped with no petiole.
*Color.*—Upper side brown (RHS (1995) closest available 200A) with burgundy hue (RHS (1995) 87A); lower side brown (RHS) (1995) 200A; midrib vein (lower side) burgundy (RHS (1995) 87A).
*Attitude.*—Upper third of plant stem: erect; mid third of plant stem: horizontal with apex tending downward; bottom third of plant stem; downward.
*Number.*—Average: 200–400.
*Arrangement.*—Tight whorls around stem.
*Veins.*—Lateral, slightly raised on upper side.
*Weather tolerance.*—Very hard, showing no signs of frost tenderness nor high temperature (or light) damage; excellent drought tolerance.
*Disease tolerance.*—Good disease tolerance, similar to *Cordyline australis.*

GENERAL CHARACTERISTICS

'Jel01' is primarily distinguished from other cultivars of *Cordyline* genus by its burgundy foliage, and shorter internode length. 'Jel01' has an upright growth habit with smooth, semi-glossy leaves with slight undulations on their margins.

What is claimed is:

1. A new and distinct *Cordyline australis* plant named 'Jel01' substantially as illustrated and described.

* * * * *